(12) United States Patent
Godony Iglesias et al.

(10) Patent No.: US 9,067,208 B2
(45) Date of Patent: Jun. 30, 2015

(54) APPARATUS FOR BLOCKING NUCLEIC ACIDS BY MEANS OF PHOTOACTIVATING INTERCALATING AGENTS

(75) Inventors: Francesc Godony Iglesias, Terrassa (ES); Jordi Morató Farreras, Terrassa (ES); Didac Sánchez Solar, Barcelona (ES)

(73) Assignee: INGENIA BIOSYSTEMS, S.L.. (ES)

( * ) Notice: Subject to any disclaimer, the term of this patent is extended or adjusted under 35 U.S.C. 154(b) by 364 days.

(21) Appl. No.: 13/502,748

(22) PCT Filed: Oct. 21, 2010

(86) PCT No.: PCT/IB2010/002696
§ 371 (c)(1),
(2), (4) Date: May 16, 2012

(87) PCT Pub. No.: WO2011/051774
PCT Pub. Date: May 5, 2011

(65) Prior Publication Data
US 2013/0045147 A1    Feb. 21, 2013

(30) Foreign Application Priority Data
Oct. 26, 2009 (ES) .................................. 200902087

(51) Int. Cl.
*B01L 9/06* (2006.01)
*B01L 3/00* (2006.01)
*C12Q 1/68* (2006.01)

(52) U.S. Cl.
CPC ............... *B01L 3/508* (2013.01); *C12Q 1/6816* (2013.01)

(58) Field of Classification Search
CPC ........... C12Q 1/6851; C12Q 2537/165; C12Q 1/6813; C12Q 2523/101; C12Q 2523/313; C12Q 2563/173; C12Q 1/6816; C12Q 1/6818; C12Q 1/6827; C12Q 1/6848; C12Q 2561/113; C12Q 1/686; B01L 3/508
See application file for complete search history.

(56) References Cited

U.S. PATENT DOCUMENTS

| 7,148,043 B2 * | 12/2006 | Kordunsky et al. ........... 435/91.2 |
| 2007/0207450 A1 | 9/2007 | Rodgers |
| 2008/0043235 A1 | 2/2008 | Oldham |
| 2009/0123959 A1 * | 5/2009 | Vesper et al. .................... 435/29 |

FOREIGN PATENT DOCUMENTS

| WO | 99/42809 A1 | 8/1999 |
| WO | 2008/070198 A2 | 6/2008 |
| WO | 2009/055810 A1 | 4/2009 |
| WO | 2011/051774 A1 | 5/2011 |

* cited by examiner

*Primary Examiner* — Sally Merkling
(74) *Attorney, Agent, or Firm* — Hess Patent Law Firm LLC; Robert J. Hess

(57) ABSTRACT

The invention relates to an apparatus for blocking nucleic acids by means of photoactivating intercalating agents, comprising:
a housing (1) with an upper wall (1a) with one or more through holes (2), intended for inserting therethrough one or more test or microcentrifuge tubes (3), each of which contains a respective sample (M) including nucleic acids and photosensitive intercalating agents mixed in liquid form, and
one or more LEDs (L1, L2, L3, L10, L20, L30) mounted inside the housing (1) such that they emit light, according to one or more determined directions, towards respective parts (3a, 3b and 3c) of said of tubes (3), to photoactivate the intercalating agents in order to covalently bond them to free or accessible nucleic acids.

16 Claims, 3 Drawing Sheets

APPARATUS FOR BLOCKING NUCLEIC ACIDS BY MEANS OF PHOTOACTIVATING INTERCALATING AGENTS

FIELD OF THE ART

The present invention relates to an apparatus for blocking nucleic acids by means of photoactivating intercalating agents using light emitting diodes, LEDs, and more particularly to an apparatus comprising a housing into which to insert one or more test or microcentrifuge tubes containing respective samples mixed with intercalating agents in liquid form, and inside which one or more LEDs which emit light towards said tube or tubes are mounted.

The present invention is comprised in the field corresponding to equipments for molecular biology techniques for the study of nucleic acids.

PRIOR STATE OF THE ART

In molecular biology techniques based on detecting nucleic acids, both in the field of diagnostics and in the field of environmental microbiology, quality control of the food industry, the pharmaceutical industry and the like, the possibility of being able to differentiate between viable cells or viruses (infectious or having pathogenic power) is very important. In all the matrices, both in clinical and environmental samples, in natural or manufactured products, there are nucleic acids of dead organisms and nucleic acids of living organisms. In all these areas, the techniques based on detecting nucleic acids are particularly important because they allow a much faster detection than most of the existing methods, and even in some cases (for example, detecting viruses) are virtually the only possibility.

Up until a few years ago, all the analytical techniques based on the study of nucleic acids were based on the study of total nucleic acids (DNA or RNA) which included both those of living organisms and those of dead organisms. This non-selective detection could condition the applicability of techniques based on DNA amplification in sectors such as quality control or diagnostics and restrict the use thereof.

Today, a new family of methods based on neutralizing free or accessible nucleic acids (which is understood as corresponding to dead organisms) with photoactivatable intercalating agents has solved the problem. Under certain light exposure conditions, these agents are photoactivated such that they bond covalently to the nucleic acids such that it invalidates them as a detection target.

It has been demonstrated today that by means of using of determined azides, such as PMA (Propidium monoazide) and EMA (Ethidium monoazide), as photoactivatable intercalating agents, it is possible to neutralize the nucleic acids of the dead cells when the reaction mixture is exposed to high voltage halogen lamps (Nogva et al., 2003; Rudi et al., 2005; Nocker, A., et al 2006; Pisz et al., 2007; Vesper et al., 2008). Even more recent studies demonstrate that PMA is a more valid option than EMA under the same conditions (Nocker et al, 2006; Flekna et al, 2007).

Regardless of the selection of the intercalating agent, in most cases today the treatment consists of a short exposure of 2 to 5 minutes to a halogen lamp of at least 650 Watts. This exposure is critical because it produces significant heating of the sample making it necessary to work with a cooling system of the samples in order to avoid damage thereto. Until now, this cooling consists of pre-cooling the sample and using ice baths. This all results in for considerable work loads the process being laborious, the temperature control not always being constant and the sample contamination risk is increased since the tube containing it is in contact with a non-sterile water-ice mass. Professionals who work with techniques of this type today do so with particular assemblies which are not based on commercial equipment.

Otherwise, it is known that intercalating agents of this type are only photoactivated with light comprised between 400-500 nm (Bolton, P. H., and Kearns, D. R., 1978), which is a very small fraction of the emission spectrum of the halogen lamps used today. Therefore the photoactivation process by itself is very inefficient.

Accordingly, commercial equipment in which it is possible to work under standard exposure conditions, minimal thermal effect and with more efficient illumination systems is necessary.

Blocking nucleic acids by means of using photosensitive intercalating agents is a developing technology. There are few published experiences today, and they are basically developed for bacteria, despite the fact that they can theoretically be applied to microorganisms of any type, such as bacteria, archaea, viruses, protozoa and other structures such as nematode eggs. Furthermore, not only should microorganisms be considered, but also the type of environmental samples (water, soil, foods) and clinical samples. It is therefore unlikely that there is a single treatment protocol. This has been the case in conventional and molecular microbiology up until now, so it is estimated that the use of agents such as PMA will require protocols adapted and developed for each type of sample and microorganism.

The photoactivation reaction depends on the concentration of the reagent and on the light dose (which is a function of time and power). In addition, the reaction must be carried out in thermal conditions which do not alter the object of the assay. For example, for psychrophilic microorganisms, the temperature increase must be minimized, and generally for all biological samples isothermal conditions assuring stability and homogeneity are required.

In pH conditions close to neutrality and for PMA, the absorption maximum is at 470 nm and said absorption presents a reduced amplitude curve, so it fits perfectly with the emission spectra of some LED models which emit blue light. There are LEDS today which allow non-continuously covering most of the visible spectrum, and even the ultraviolet spectrum. So for photo-biochemical laboratory and industrial-scale processes, they are usually the most logical option due to the light quality and their performance efficiency.

Application WO2009055810-A1 describes a proposal which contemplates carrying out the mentioned photoactivation by means of blue light, particularly using LEDs. Said application describes a microorganism discriminator comprising a housing for incubating the sample in low-light conditions, including an injector arranged in the housing to supply the intercalating agents (for example PMA) to the sample, and an illuminator to emit blue light towards the sample. Although said application includes an independent claim which does not include a base for transporting the sample between the housing and the illuminator, and vice-versa, in all the embodiments described, the microorganism discriminator of WO2009055810-A1 comprises said base since the incubating housing and the illuminator are two separate units. Said application does not propose implementing the entire photoactivation process in a single apparatus or applying it on samples mixed in liquid form with the intercalating agents in test or microcentrifuge tubes.

Most microbiological assay procedures have many steps, many of which are based on the metering of liquid reagents, and the samples are processed by means of dissolving in isotonic solutions. In this scenario, most published assays, with the exception of the one described by Vesper et al., 2008 in "Quantifying fungal viability in air and water samples using quantitative PCR after treatment with propidium monoazide (PMA)", J. Microbiol. Methods. 72, 180-184, associated with application WO2009055810-A1, are based on processing the samples and metering PMA in liquid and in microcentrifuge tubes, although not by means of LEDs. It is therefore considered as more appropriate that equipment intended for assays of this type has microcentrifuge tubes as a working support.

SUMMARY OF THE INVENTION

It is necessary to offer an alternative to the state of the art which covers the gaps found therein, particularly those relating to the inexistence of proposals which allow, by means of a single apparatus, photoactivating a sample with intercalating agents mixed in liquid form in a test or microcentrifuge tube by means of LEDs.

For providing such proposal, which has been inexistent up until now, the present invention relates to an apparatus for blocking nucleic acids by means of photoactivating intercalating agents, of the type comprising:

a housing to house one or more samples including nucleic acids and photosensitive intercalating agents, generally PMA or EMA, and one or more light emitting diodes, LEDs, arranged to emit light towards said sample or samples, to photoactivate said intercalating agents in order to covalently bond them to at least part of said nucleic acids.

Unlike conventional proposals, particularly unlike the one described in WO2009055810-A1, the housing of the apparatus provided by the present invention comprises a wall with one or more through holes, each of them intended for inserting therethrough, at least in part, a respective test or microcentrifuge tube containing said sample and said intercalating agents mixed in liquid form, at least one of said LED or LEDs being mounted inside the housing in order to emit light, in a determined direction, towards part of said test or microcentrifuge tube including said sample.

It is known that LED emitters, including high-powered emitters, are small devices which emit light with an aperture which is a function of the structure thereof, and in absolute terms they are low-powered devices. Therefore, the use of the latter generally requires the combination of several units, it being necessary to contemplate the arrangement thereof with respect to one another and to the object to be illuminated. The objective is to achieve the greatest exposed surface with the necessary intensity and preventing the existence of non-illuminated areas. On the other hand, it is still necessary to contemplate a minimum distance with respect to the object to be illuminated which minimizes a thermal effect due to the LEDs (and the associated electronics).

As a result, for one embodiment said wall of said housing comprises a plurality of through holes intended for inserting therethrough, at least in part, a corresponding plurality of test or microcentrifuge tubes, each of which contains a respective sample and intercalating agents mixed in liquid form, and the apparatus comprises a plurality of said LEDs mounted inside said housing such that they emit light, in at least one determined direction, towards respective parts of said plurality of test or microcentrifuge tubes including said respective samples, at least one LED per tube.

For one embodiment, said plurality of LEDs comprises at least several first LEDs, each of them arranged adjacent to the tip of a respective one of said test or microcentrifuge tubes, to emit light towards it in said determined direction which coincides with the longitudinal axis of the tube.

Equipment which has the purpose of treating biological samples with agents such as PMA must assure optimal performance of all the optics in order to maximize the irradiation of the support to be treated, while at the same time it must allow the operator to adjust the light dose in a thermally stable environment compatible with the object of the assay.

In order to achieve this optimal performance assurance, for one embodiment the apparatus provided by the present invention comprises a plurality of LEDs with suitable optics (built-in or external to the LEDs) designed for such purpose, as well as manual and/or automatic adjustment means to regulate the light emitted by the LEDs. The mentioned thermally stable environment is achieved by means of a venting system formed by one or more fans by means of which the LEDs and the whole inside of the housing, including the sample, are cooled, which venting system is comprised in the apparatus provided by the invention for one embodiment.

BRIEF DESCRIPTION OF THE DRAWINGS

The foregoing and other advantages and features will be more fully understood from the following detailed description of several embodiments with reference to the attached drawings, which must be interpreted in an illustrative and non-limiting manner, in which.

DETAILED DESCRIPTION OF SEVERAL EMBODIMENTS

Figure 1:
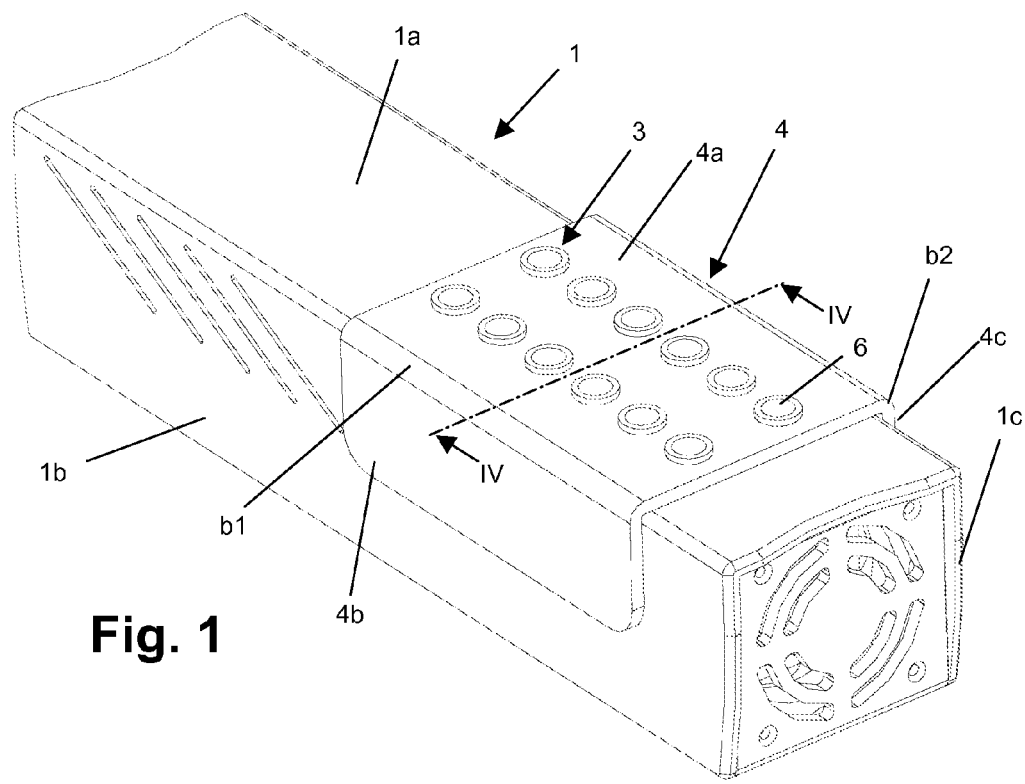
FIG. 1 is a perspective view of the apparatus provided by the present invention with a series of microcentrifuge tubes held by a support and partially inserted inside the housing of the apparatus for one embodiment.

As is seen in the attached figures, the apparatus for blocking nucleic acids by means of photoactivating intercalating agents provided by the present invention comprises, for the illustrated embodiment:

a housing 1 which forms a parallelepiped body with an upper wall 1a with a plurality of through holes 2, particularly twelve (see FIG. 2), intended for inserting therethrough a corresponding plurality of microcentrifuge tubes 3, each of which contains a respective sample M (see FIG. 4) including nucleic acids and photosensitive intercalating agents mixed in liquid form, and a plurality of LEDs L1, L2, L3, L10, L20, L30, (see FIGS. 4 and 5) mounted inside the housing 1 such that they emit light, according to different determined directions, towards respective parts 3a, 3b and 3c of said plurality of test or microcentrifuge tubes 3, to photoactivate the intercalating agents in order to covalently bond them to at least part of said nucleic acids, particularly to the free or accessible nucleic acids.

For a preferred embodiment, the LEDs L1, L2, L3, L10, L20, L30 are configured to emit a blue light in a range of 400 to 500 nm.

For the illustrated embodiment, the housing 1 is formed by two parts that can be coupled to one another to form said parallelepiped body: one (see FIGS. 1 and 2) comprising said upper wall 1a and larger side walls 1b, 1c, and another one (see FIGS. 3 and 5) comprising a base wall 1d, opposite said upper wall la when both parts of the housing 1 are coupled, and two smaller side walls 1e, 1f.

Figure 2:
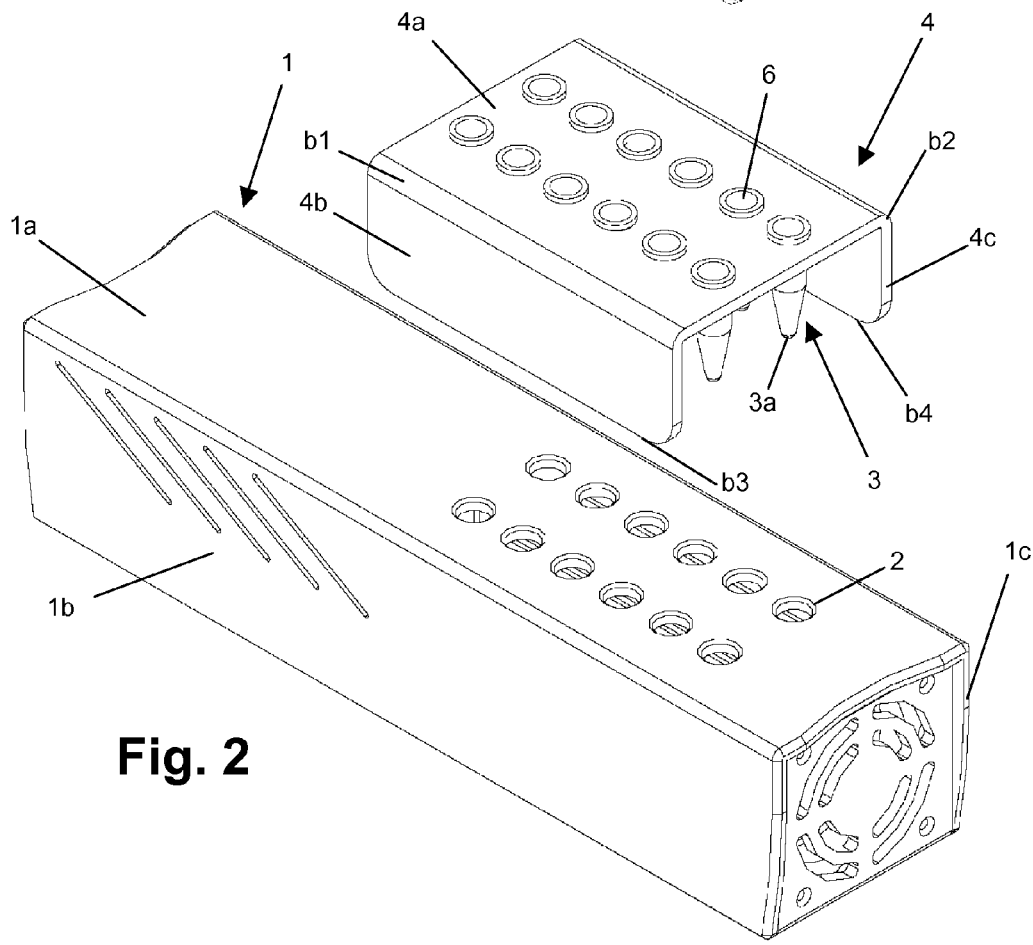
FIG. 2 is a view analogous to that of FIG. 1 but in which the support with the microcentrifuge tubes is shown in an exploded view with respect to the rest of the apparatus.

As is seen in FIGS. 1 and 2, the apparatus provided by the present invention comprises a support 4 for said plurality of microcentrifuge tubes 3, intended for, when arranged adjacent to the upper wall la of the housing 1, positioning each of the microcentrifuge tubes 3 in relation to a respective hole of said plurality of through holes 2 and enabling their insertion therein/extraction therefrom.

It can be seen in said FIGS. 1 and 2 that the support 4 comprises a board 4a defining a corresponding plurality of through holes 5 with a diameter less than the diameter of the outer contour of an area close to the opening of each microcentrifuge tube 3 or of a stopper 6 closing such opening (illustrated case), such that each of the tubes 3 is fitted in one of the through holes 5 upon passing through it in part, being held in this case by the lower contour of each stopper 6 (see FIG. 4), the through holes 5 being distributed in the same manner as the through holes 2 of the upper wall 1a of the housing 1, in this case forming two rows of six holes, being aligned therewith when said board 4a is arranged adjacent on the area of the upper wall 1a of the housing 1 including the through holes 2, as is seen in the situation illustrated in FIG. 1. In other words, the tubes 3 are positioned by means of the support 4 when introducing them in the housing 1 through the holes 2.

Figure 4:
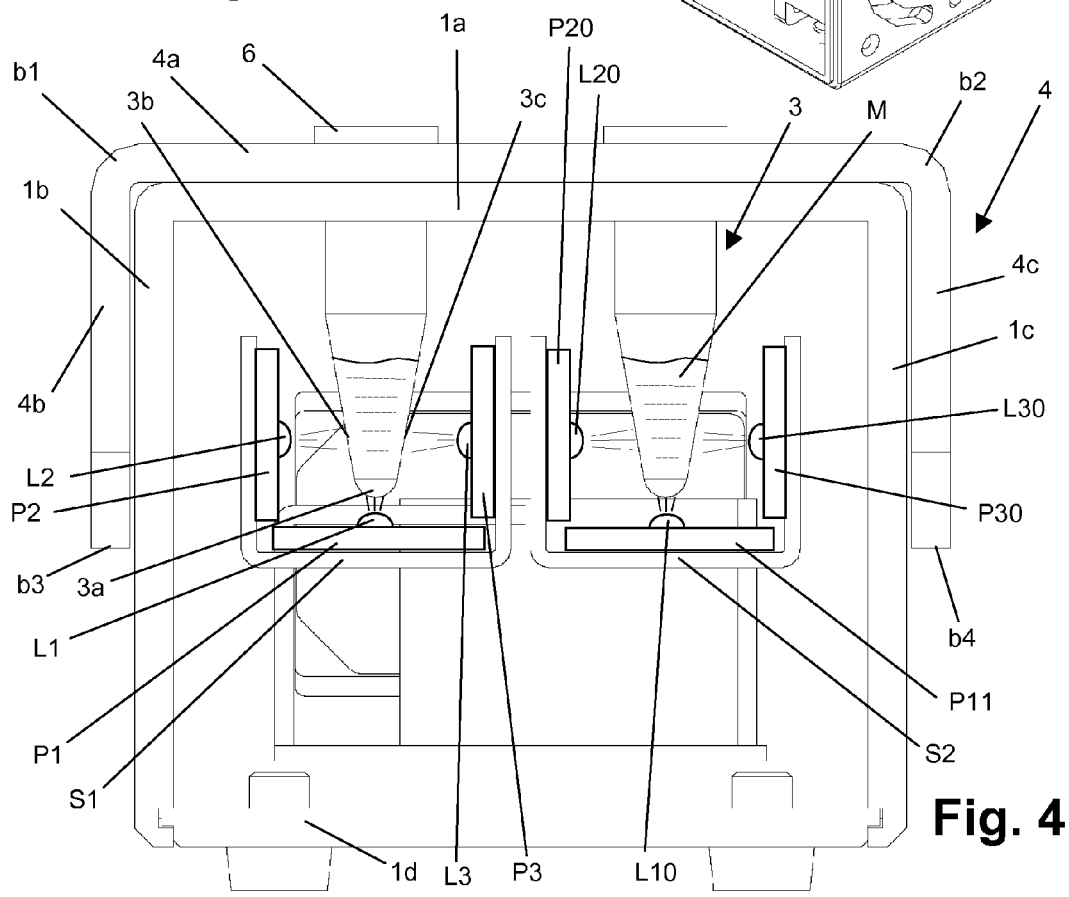
FIG. 4 is a cross-section view of the apparatus provided by the present invention according to a section made through a plane indicated as section line IV-IV in FIG. 1.

The support 4 illustrated in FIGS. 1, 2 and 4 comprises two side walls 4b, 4c extending from two respective longitudinal edges b1, b2 of the board 4a, the support 4 adopting a U-shaped cross-section, and it can be seen that when the board 4a is arranged adjacent to the upper wall 1a of the housing 1 (situation illustrated in FIG. 1), each of said two side walls 4b, 4c of the support 4 is adjacent to a region of a respective one of two larger side walls 1b, 1c of the housing 1, simply contacting them if the support 4 is only to be supported on the housing 1, or exerting slight pressure against them (for example by elastic deformation) if the support 4 is to be detachably fixed to the housing 1, depending on the embodiment.

It can particularly be seen in FIG. 4 that the distance of the side walls 4b, 4c going from the longitudinal edge b1, b2 of the board 4a to its free edge b3, b4, opposite said longitudinal edge b1, b2, is greater than the longitudinal portion of the microcentrifuge tube 3 which passes through the through hole 5 of the board 4a of the support 4, such that when the support 4 is supported on a flat surface by said free edges b3, b4, the tips 3a of the test or microcentrifuge tubes 3 do not touch said flat surface.

Figure 5:
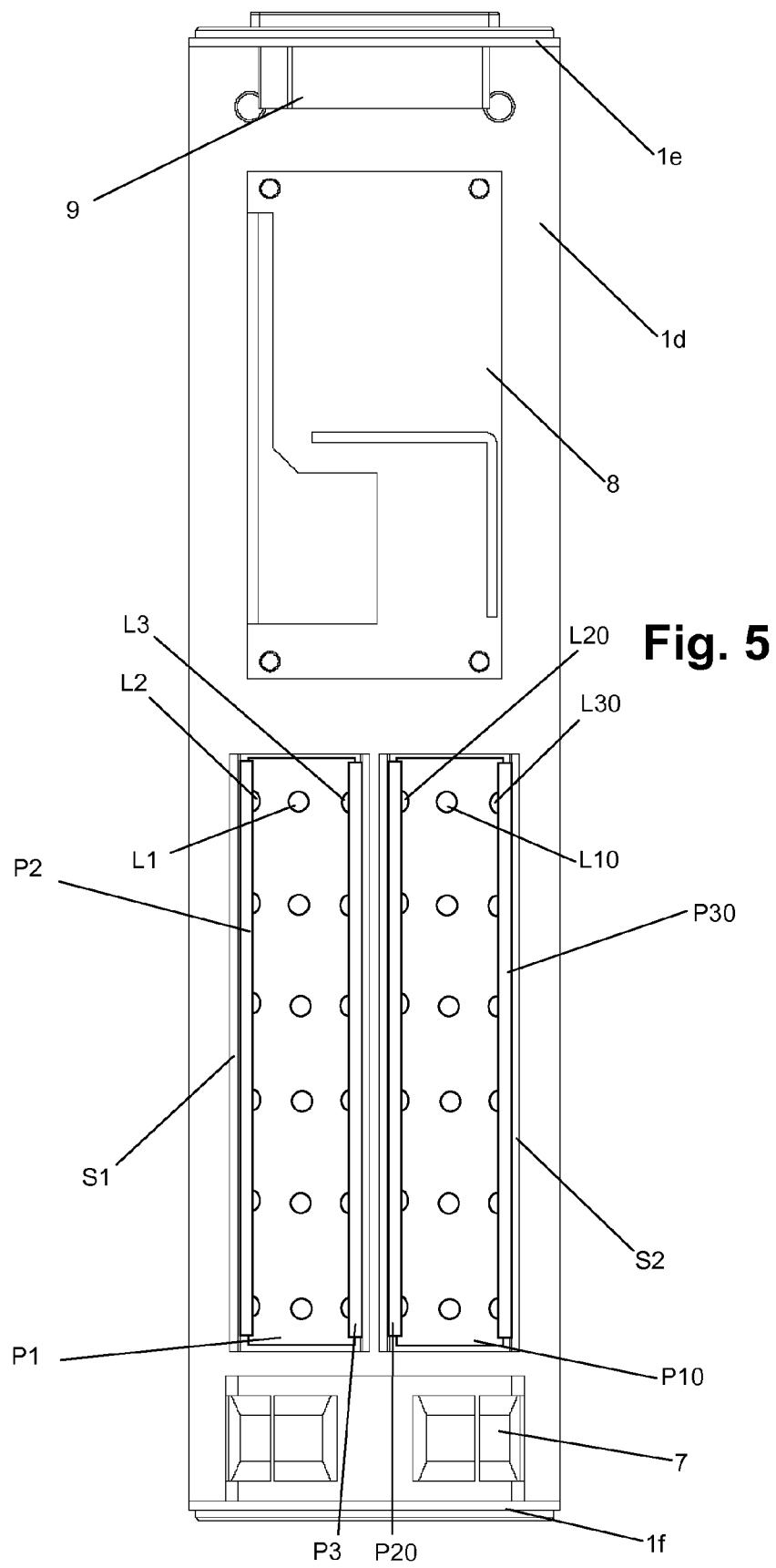
FIG. 5 shows a plan view of part of the elements mounted inside the apparatus provided by the present invention.

As is shown in FIG. 5, the mentioned plurality of LEDs is formed by six rows of LEDs, three per row of tubes 3. Although only one LED of each of said rows has been indicated in FIG. 5, respectively, by references L1, L2, L3, L10, L20, L30, it must be understood that said references seek to point out each of the LEDs of each respective row, i.e., for example, L1 refers to each of the LEDs of the row to which the LED pointed out by said reference in FIG. 5 belongs.

It is observed in the sectional view shown in FIG. 4 how the apparatus provided by the invention comprises:

several first LEDs L1, L10, particularly two rows of LEDs, each of them arranged adjacent to the tip 3a of a respective one of microcentrifuge tubes 3, to emit light towards it in a determined direction which coincides with the longitudinal axis of the tube 3.

several second LEDs L2, L20, also forming two rows of LEDs, each of them mounted inside the housing 1 being arranged adjacent to a first side wall region 3b of a respective one of said microcentrifuge tubes 3, said region 3b being included in the longitudinal third thereof ending in a respective one of said tips 3a, to emit light towards it in a transverse direction, and several third LEDs L3, L30, clustered in two rows, each of them mounted inside the housing 1 being arranged adjacent to a second side wall region 3c of a respective one of said test or microcentrifuge tubes 3, opposite said first region 3b, and therefore also included in the longitudinal third of the tube 3 ending in a respective one of said tips 3a, to emit light towards it also in a transverse direction.

With the described LED arrangement, uniform illumination of the part of each tube 3 in which the sample M is housed (particularly the mentioned longitudinal third of the tube 3 ending in the tip 3a) is achieved, such that all the intercalating agents included in each sample M are photoactivated.

The apparatus provided by the invention comprises an electronic system including the LEDs L1, L2, L3, L10, L20, L30 mounted on printed circuit boards P1, P2, P3, P10, P20, P30 (six in FIGS. 4 and 5, one per row of LEDs) with electric/electronic circuitry electrically connected thereto.

In FIGS. 4 and 5 it can be seen how the boards of each group of three printed circuit boards, P1, P2, P3, on one side, and P10, P20, P30, on the other, associated with a respective one of the two rows of tubes 3, are mounted on a respective support element S1, S2, such that the LEDs L1, L2, L3, L10, L20, L30 are at a certain distance from the microcentrifuge tubes 3, which distance is predetermined to meet the minimum distance requirements, mentioned in a previous section, which are necessary for minimizing a thermal effect due to the LEDs (and the associated circuitry) on the samples M.

Figure 3:
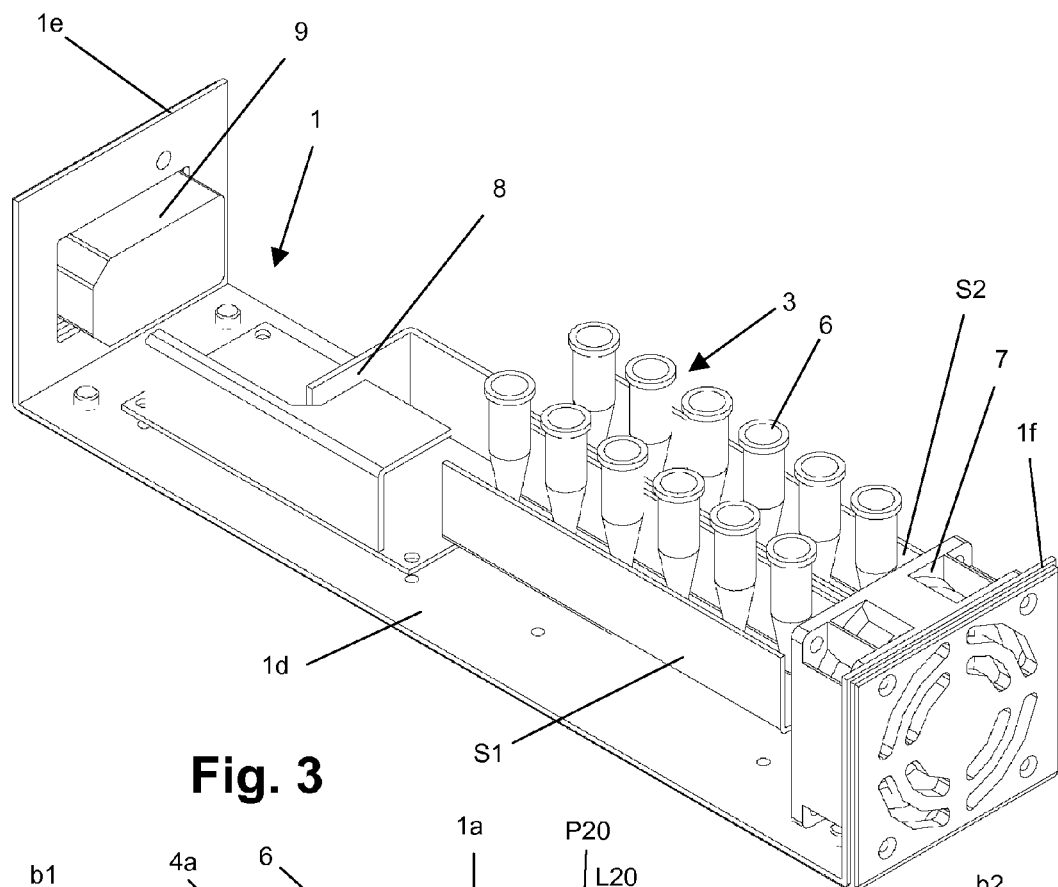
FIG. 3 shows a perspective view of the inside of the apparatus of FIG. 1 with the microcentrifuge tubes illustrated as they are positioned with the aid of the support illustrated in FIGS. 1 and 2.

FIGS. 3 and 5 schematically show a power supply 8 (the components forming it have been omitted in the illustration as they are conventional) and a plug 9 for the supply through the electrical network, the power supply being connected to the plug 9 and to the electronic system (connections not illustrated) for the purpose of supplying the latter with the suitable operating voltage once that coming from the network has been treated.

The mentioned electronic system is intended for controlling the operation of the LEDs L1, L2, L3, L10, L20, L30 in order to regulate their different operating parameters, from the light intensity with which to emit to the time and mode of emission.

For an embodiment that has not been illustrated, the apparatus comprises one or more manual controls connected to the electronic system so as to allow the user to participate in said control of the operation of the LEDs, such that this can be done manually or automatically, according to the application.

In FIGS. 3 and 5 it can be seen how the apparatus provided by the present invention comprises a venting system formed by a fan 7 mounted inside the housing 1 facing towards the LEDs L1, L2, L3, L10, L20, L30 for the purpose of cooling them and thus maintaining the mentioned thermally stable environment.

A person skilled in the art could introduce changes and modifications in the embodiments described without departing from the scope of the invention as it is defined in the attached claims.

The invention claimed is:

1. An apparatus for blocking nucleic acids in a manner that covalently bonds the photoactivated intercalating agents with at least part of nucleic acids, comprising:
   a housing with outer perimeter walls demarcating an inner enclosure for housing a test or microcentrifuge tube containing at least one sample including nucleic acids and photosensitive intercalating agents mixed in liquid form, wherein at least one of said outer perimeter walls has at least one through-hole completely traversing a thickness of said outer perimeter wall and dimensioned for accommodating insertion there through at least in part the test or microcentrifuge tube containing the at least one sample including the nucleic acids and the photosensitive intercalating agents mixed in the liquid form;
   a removable test or microcentrifuge tube containing at least one sample including nucleic acids and photosensitive intercalating agents mixed in liquid form, wherein said test or microcentrifuge tube is inserted through said throughhole such that at least part of the test or microcentrifuge tube is arranged within said inner enclosure; and
   light emitting means for photoactivating said photosensitive intercalating agents in a manner that covalently bonds said photosensitive intercalating agents to at least part of said nucleic acids, said light emitting means including at least one light emitting diode (LED) arranged to emit light towards said at least one sample in the manner that photoactivates said intercalating agents to covalently bond said photosensitive intercalating agents to at least part of said nucleic acids, and said at least one LED being mounted inside said inner enclosure of said housing and arranged with respect to said at least one through hole and with respect to said at least one test or microcentrifuge tube such that said at least one LED emits light, in a determined direction, towards a portion of the at least one test or microcentrifuge tube, said portion including said sample and said intercalating agents mixed in the liquid form.

2. The apparatus according to claim 1, wherein said at least one outer perimeter wall of said housing comprises a plurality of throughholes and a corresponding plurality of test or microcentrifuge tubes inserted there through, each of which contains a respective sample including nucleic acids and photosensitive intercalating agents mixed in liquid form, the apparatus comprising a plurality of said LEDs mounted inside said inner enclosure of said housing such that they emit light, in at least one determined direction, towards respective portions of said plurality of test or microcentrifuge tubes, at least one LED per tube, including said respective samples.

3. The apparatus according to claim 2, wherein said plurality of LEDs comprises at least several first LEDs, each of them arranged adjacent to the tip of a respective one of said test or microcentrifuge tubes, to emit light towards said tip in said determined direction which coincides with the longitudinal axis of the test or microcentrifuge tube.

4. The apparatus according to claim 3, wherein said plurality of LEDs further comprises several second LEDs, each of them mounted inside the inner enclosure of the housing being arranged adjacent to a first side wall region of a respective one of said test or microcentrifuge tubes, to emit light towards said first side wall region in a transverse direction, and at least several third LEDs, each of them mounted inside the housing being arranged adjacent to a second side wall region of a respective one of said test or microcentrifuge tubes, opposite said first region, to emit light towards said second side wall region also in a transverse direction.

5. The apparatus according to claim 4, wherein said second LEDs and third LEDs are arranged to emit light towards side wall regions of each test or microcentrifuge tube included in an end portion thereof covering a third of its length, said end portion ending in a respective one of said tips.

6. The apparatus according to claim 2, further comprising a removable support for said plurality of test or microcentrifuge tubes, removably arranged adjacent to an outer face of said outer perimeter wall of the housing comprising said plurality of through-holes, said support positioning each of the test or microcentrifuge tubes in relation to a respective hole of said plurality of through-holes and enabling its insertion therein/extraction therefrom.

7. The apparatus according to claim 6, wherein said outer perimeter wall is an upper outer perimeter wall of the housing, and said support comprises a board defining a corresponding plurality of through-holes with a diameter less than the diameter of the outer contour of an area close to the opening of each test or microcentrifuge tube or of a stopper closing such opening to allow that each of the test or microcentrifuge tubes be fitted in one of said through-holes of the support upon passing through it only in part, specifically until said area close to the opening or said stopper interferes with said board, said through-holes being distributed in the same manner as the through-holes of the upper wall of the housing, being aligned therewith upon said board being arranged adjacent on the area of the upper wall of the housing including said through-holes.

8. The apparatus according to claim 7, wherein said housing is a parallelepiped body, formed by said outer perimeter walls, and said removable support comprises two side walls extending from two respective longitudinal edges of said board, the support adopting a U-shaped cross-section, each of said two side walls of the support being adjacent to a region of a respective one of two larger side outer perimeter walls of the housing.

9. The apparatus according to claim 8, wherein the distance of said two side walls of the removable support going from the longitudinal edge of the board to its free edge opposite said longitudinal edge is greater than at least the longitudinal portion of the test or microcentrifuge tube which passes through said through-hole of the board of the support.

10. The apparatus according to claim 2, comprising an electronic system including said LEDs mounted on at least one printed circuit board with electric/electronic circuitry electrically connected thereto.

11. The apparatus according to claim 10, wherein said at least one printed circuit board is mounted on a support element fixedly arranged in said inner enclosure, with no relative movement thereto, such that the LEDs are at a certain distance from the test or microcentrifuge tubes.

12. The apparatus according to claim 11, wherein said electronic system is configured for controlling the operation of said LEDs.

13. The apparatus according to claim 2, wherein said LEDs are configured to emit a blue light in a range of 400 to 500 nm.

14. The apparatus according to claim 2, comprising a cooling venting system formed by at least one fan mounted inside said inner enclosure of the housing facing towards said LEDs.

15. The apparatus according to claim 1, wherein said housing is formed by two parts that removably coupled to one another to form said parallelepiped body: one comprising said upper outer perimeter wall and said larger side outer perimeter walls, and the other one comprising a base outer perimeter wall, opposite said upper outer perimeter wall, and two smaller side outer perimeter walls orthogonal to said larger side outer perimeter walls.

16. An apparatus for blocking nucleic acids in a manner that covalently bonds the photoactivated intercalating agents with at least part of nucleic acids, comprising:

a housing with outer perimeter walls demarcating an inner enclosure for housing a test or microcentrifuge tube containing at least one sample including nucleic acids and photosensitive intercalating agents mixed in liquid form, wherein at least one of said outer perimeter walls has at least one through-hole completely traversing a thickness of said outer perimeter wall and dimensioned for accommodating insertion there through at least in part the test or microcentrifuge tube containing the at least one sample including the nucleic acids and the photosensitive intercalating agents mixed in the liquid form; and light emitting means for photoactivating said photosensitive intercalating agents in a manner that covalently bonds said photosensitive intercalating agents to at least part of said nucleic acids, said light emitting means including at least one light emitting diode (LED) arranged to emit light towards said at least one sample in the manner that photoactivates said intercalating agents to covalently bond said photosensitive intercalating agents to at least part of said nucleic acids, wherein said at least one LED is mounted inside said inner enclosure of said housing and arranged with respect to said at least one through-hole such that as said test or microcentrifuge tube is inserted there through, from the exterior of the inner enclosure, said at least one LED emits light, in a determined direction, towards an inner region of the inner enclosure occupied by a portion of said at least one test or microcentrifuge tube, said portion including said sample and said intercalating agents mixed in the liquid form.

* * * * *